US012694954B2

(12) United States Patent
Li et al.

(10) Patent No.: US 12,694,954 B2
(45) Date of Patent: Jul. 28, 2026

(54) METHOD FOR GENERATING SMALL MOLECULE BASED ON PHARMACOPHORE MODEL, DEVICE, AND MEDIUM

(71) Applicant: Central South University, Changsha (CN)

(72) Inventors: Min Li, Changsha (CN); Renyi Zhou, Changsha (CN); Huimin Zhu, Changsha (CN)

(73) Assignee: Central South University, Changsha (CN)

( * ) Notice: Subject to any disclaimer, the term of this patent is extended or adjusted under 35 U.S.C. 154(b) by 484 days.

(21) Appl. No.: 18/279,032

(22) PCT Filed: Dec. 2, 2022

(86) PCT No.: PCT/CN2022/136051
§ 371 (c)(1),
(2) Date: Aug. 25, 2023

(87) PCT Pub. No.: WO2023/226351
PCT Pub. Date: Nov. 30, 2023

(65) Prior Publication Data
US 2025/0014687 A1 Jan. 9, 2025

(30) Foreign Application Priority Data
May 27, 2022 (CN) .......................... 202210584466.5

(51) Int. Cl.
*G16C 20/50* (2019.01)
*G06N 3/042* (2023.01)
(Continued)

(52) U.S. Cl.
CPC ............. *G16C 20/50* (2019.02); *G06N 3/042* (2023.01); *G06N 3/0455* (2023.01); *G16C 20/70* (2019.02)

(58) Field of Classification Search
CPC ........ G16C 20/50; G16C 20/70; G06N 3/042; G06N 3/0455
See application file for complete search history.

(56) References Cited

U.S. PATENT DOCUMENTS 10,776,712 B2 * 9/2020 Oono ..................... G06N 20/00
11,263,534 B1 * 3/2022 Prat ......................... G06N 5/022
(Continued)

OTHER PUBLICATIONS

Constrained Graph Variational Autoencoders for Molecule Design, Qi Liu, Miltiadis Allamanis, Marc Brockschmidt, and Alexander L. Gaunt Singapore University of Technology and Design, Microsoft Research, Cambridge (Year: 2018).*
(Continued)

*Primary Examiner* — Barbara M Level
(74) *Attorney, Agent, or Firm* — PEARL COHEN ZEDEK LATZER BARATZ LLP

(57) ABSTRACT

The present disclosure provides a method for generating a small molecule based on a pharmacophore model, a device, and a medium. The method includes: using a fully connected graph to represent a pharmacophore model; using a feature extraction model based on a graph neural network to extract a feature vector of the pharmacophore model from the fully connected graph of the pharmacophore model; performing random sampling on a specified latent variable distribution to obtain a latent variable; and inputting the latent variable and the feature vector of the pharmacophore model to a pre-trained decoder to generate a molecule matching the pharmacophore model, where the pre-trained decoder is a decoder obtained by training a variational autoencoder with training samples.

17 Claims, 3 Drawing Sheets

(51) Int. Cl.
    *G06N 3/0455*     (2023.01)
    *G16C 20/70*      (2019.01)

(56)            References Cited

U.S. PATENT DOCUMENTS

| | | | | |
|---|---|---|---|---|
| 11,481,549 | B2 * | 10/2022 | McCarthy | G06F 40/253 |
| 11,610,139 | B2 * | 3/2023 | Bucher | G06N 3/0475 |
| 12,367,397 | B2 * | 7/2025 | Hoffman | G06F 16/245 |
| 12,462,902 | B2 * | 11/2025 | Lee | G06N 3/08 |
| 2020/0090049 | A1 * | 3/2020 | Aliper | G06N 3/088 |
| 2020/0176087 | A1 * | 6/2020 | Colby | G06N 3/088 |
| 2022/0208540 | A1 * | 6/2022 | Behsaz | G06N 3/0464 |
| 2022/0230713 | A1 * | 7/2022 | Maragakis | G06N 3/0475 |
| 2023/0083810 | A1 * | 3/2023 | Xu | G16C 20/90 |
| | | | | 703/11 |
| 2023/0154573 | A1 * | 5/2023 | Roy | G16B 15/30 |
| | | | | 702/27 |
| 2023/0352123 | A1 * | 11/2023 | Atkinson | G06N 3/084 |
| 2023/0420069 | A1 * | 12/2023 | Stojevic | G16B 5/00 |
| 2024/0428065 | A1 * | 12/2024 | Kishimoto | G06N 3/044 |

OTHER PUBLICATIONS

Pietro Bongini, Monica Bianchini, Franco Scarselli, Molecular
generative Graph Neural Networks for Drug Discovery, Neurocomput-
ing, vol. 450, pp. 242-252, ISSN 0925-2312, https://doi.org/10.1016/
j.neucom.2021.04.039. (https://www.sciencedirect.com/science/
article/pii/S0925231221005737) (Year: 2021).*

* cited by examiner

METHOD FOR GENERATING SMALL MOLECULE BASED ON PHARMACOPHORE MODEL, DEVICE, AND MEDIUM

CROSS REFERENCE TO RELATED APPLICATION

This patent application is a national stage application of International Patent Application No. PCT/CN2022/136051, filed on Dec. 2, 2022, which claims the benefit and priority of Chinese Patent Application No. 202210584466.5 filed with the China National Intellectual Property Administration on May 27, 2022 and entitled "METHOD FOR GENERATING SMALL MOLECULE BASED ON PHARMACOPHORE MODEL, DEVICE, AND MEDIUM", the disclosure of which is incorporated by reference herein in its entirety as part of the present application.

TECHNICAL FIELD

The present disclosure relates to the technical field of research and development of drugs, and in particular, to a method for generating a small molecule based on a pharmacophore model, a device, and a medium.

BACKGROUND

The research and development of a new drug may be a project which is long in time period, tremendous in cost, high in risk, and low in success rate. Drug discovery goes through four processes: determination of a relevant target, discovery of a lead compound, optimization of properties of the lead compound, and determination of a candidate drug. The determination of a lead compound having potential is a key step of the drug discovery. The lead compound is a compound having a certain biological activity and a chemical structure which is not necessarily optimal. The lead compound may be subjected to structural alteration and modification for optimization of physical and chemical properties thereof, thereby further obtaining a candidate drug. Accordingly, the lead compound is the starting point of modern new drug research. The traditional discovery of a lead compound is mainly to discover a first compound having an activity to a given biologic object by screening from a chemical library, screening from naturally separated materials (e.g., plants, bacteria, and fungi), or through a computer simulation process. The druggable potential of a molecule is preliminarily determined by using the experience of a pharmaceutical chemist, and the binding activity of the molecule is tested by using an experimental means. A huge chemical space and an experimental cost contribute to the disadvantages of low efficiency, high cost, and low success rate of traditional drug research and development. Therefore, how to rapidly and accurately obtain a lead compound is an important step of drug research and development.

A generative model, as a powerful data-driven reverse design method, has gained attention recently. The generative model learns a distribution of molecules through powerful feature extraction capability and fitting capability of deep learning and then obtains a new molecule by sampling from the learned distribution. By appropriately limiting the distribution, a molecule having an expected property may be generated. Many relevant efforts have been made at present. A great majority of generative models focus on the physical and chemical properties of generated molecules, such as lipid solubility, molecular weight, and synthesis difficulty level. There are few methods with a molecular activity as a generation object. This is because of the scarcity of data for active molecules towards a specific target or the high-resolution structure of the target and the difficulty for a model to learn a joint probability distribution of structures and activities. For a new target family, the deficiency of available activity data is even more obvious. Therefore, it is a key task to combine a deep generative model with the knowledge of the field of biochemistry and effectively utilize scarce active molecule data to design a bioactive molecule. Few methods with an active molecule as a design object, such as a fragment-based drug design method and a target structure-based three-dimensional molecular structure design method, are limited to drug design scenarios with unknown binding sites or unknown protein structures.

Combining the prior knowledge of a biochemist with a molecular generative model is conducive to effectively designing a drug. A pharmacophore model is a set of functional group features and spatial information of a binding site where a compound is bound to the target. There have been many successful cases for pharmacophore based drug design. A pharmacophore model mainly includes two parts. A first part is pharmacophore features reflected by atoms or groups. The first part typically includes a hydrogen bond donor, a hydrogen bond receptor, an aromatic ring, a hydrophobic core, a positive charge center, and a negative charge center. A second part is spatial information of each pharmacophore feature. The utilization of the pharmacophore in drug design has many advantages: 1) the pharmacophore model provides a powerful artificial prior for generating a target molecule. Through the pharmacophore features, a biologically significant molecule matching the given pharmacophore model can be effectively generated using the knowledge of a biochemist. 2) The pharmacophore model is a succinct expression of a molecularly active site, and designing a molecule on this basis is beneficial to generate a drug-like molecule having diverse structures. An existing generative model incorporating with relevant features of a pharmacophore model uses only partial information of the pharmacophore model. For example, partial pharmacophore feature information is added as limitations to the model. These methods cannot generate a molecule only according to a pharmacophore model and requires extra information such as an active fragment, and therefore, their usage scenarios are limited.

SUMMARY

The present disclosure provides a method for generating a small molecule based on a pharmacophore model, a device, and a medium, so that information contained in pharmacophore model can be comprehensively utilized to generate an active molecule for a target with few biomolecules or a new target family.

To achieve the above objective, the present disclosure adopts the following technical solutions.

A method for generating a small molecule based on a pharmacophore model includes:

step 1, using a fully connected graph to represent a pharmacophore model;

step 2, using a feature extraction model based on a graph neural network to extract a feature vector of the pharmacophore model from the fully connected graph of the pharmacophore model;

step 3, performing random sampling on a specified prior distribution of latent variables to obtain a latent variable; and

step 4, inputting the latent variable and the feature vector of the pharmacophore model to a pre-trained decoder to generate a molecule matching the pharmacophore model;

where the pre-trained decoder is a decoder obtained by training a variational autoencoder with training samples; and the variational autoencoder is expressed as:

$$P(x|c) = \int_{z \sim P(z|c)} P(x|c,z) P(z|c) dz;$$

where $P(x|c)$ represents the variational autoencoder, and $P(z|c,x)$ and $P(x|c,z)$ represent an encoder and a decoder forming the variational autoencoder, respectively; x represents a molecule, which is uniquely encoded as a combination of the feature vector c of the pharmacophore model and a latent variable z; and the latent variable z represents a way of the pharmacophore model mapping to the molecule, namely how chemical components in the pharmacophore model express and are combined into the molecule.

Further, the variational autoencoder includes an encoder, a decoder, a prior distribution of latent variables, and a loss function; the training samples for training the variational autoencoder include the feature vector of the pharmacophore model and the molecule matching the pharmacophore model; upon training the variational autoencoder with the training samples:

the feature vector of the pharmacophore model and the molecule matching the pharmacophore model are input to the encoder to obtain a latent variable distribution of the molecule with respect to the pharmacophore model;

a latent variable is sampled from the latent variable distribution output from the encoder, and the feature vector of the pharmacophore model and the sampled latent variable are input to the decoder to generate a molecule by an iterative loop;

the prior distribution of latent variables is used for performing minimal optimization on a difference between the latent variable distribution obtained by the encoder during training and a given prior distribution; and the loss function is used for quantizing a difference between the molecule generated by the decoder and the molecule in the training samples. Further, the loss function includes but is not limited to two parts; an expression of a first part is $-KL(P_\varphi(z|x,c) \| P_\theta(z|c))$, where $\varphi$ represents a decoder parameter, and $\theta$ an encoder parameter, z the latent variable, x the molecule, c the pharmacophore model, and KL Kullback-Leibler divergence; and an expression of a second part is $\log P_\theta(x|z,c)$.

Further, the encoder and the decoder are based on a Transformer architecture.

Further, the using a fully connected graph to represent a pharmacophore model specifically includes forming the fully connected graph of the pharmacophore model with each pharmacophore feature included in the pharmacophore model as a node and associated information between pharmacophore features as an edge, where a node feature includes but is not limited to a type and a shape of the pharmacophore feature.

Further, a length of a shortest path between the pharmacophore features is used to represent an association relationship between the pharmacophore features.

Further, the given prior distribution is specifically a standard normal distribution.

Further, the molecule in the training samples and the molecule generated in step 4 are expression forms obtained after performing an original molecule by using a simplified molecular input line entry specification (SMILES).

An electronic device includes a memory in which a computer program is stored, and a processor, where the computer program, when executed by the processor, causes the processor to implement the method for generating a small molecule as described in any of the above technical solutions.

A computer-readable storage medium stores a computer program thereon, where the computer program, when executed by a processor, implements the method for generating a small molecule.

Beneficial Effects

Compared with the prior art, the present disclosure has the following beneficial effects: the present disclosure guides the generation of a molecule by using the pharmacophore model, and in combination with the professional knowledge of chemical biologists, data is utilized efficiently to solve the problem of active molecule generation when lacking experimental data for a particular target. The generative model utilizes the variational autoencoder framework and improves the structural diversity of the generated molecule. The model is flexible and only needs to be trained once before being applied to drug design tasks in different scenarios. The present disclosure can be applied to ligand-based drug design, receptor-based drug design, lead compound optimization, finding an alternative for drug resistance, and establishing a molecular database for virtual screening to replace molecular screening of a large-scale federated database, and can reduce blind trial work, save the time and cost of drug research and development, and relieve the pressure of drug research and development.

DETAILED DESCRIPTION OF THE EMBODIMENTS

Embodiments of the present disclosure will be described below in detail. The embodiments are carried out on the basis of the technical solutions of the present disclosure, and detailed implementations and specific operation processes are given to further explain the technical solutions of the present disclosure.

To make the method, features, advantages, and application of the present disclosure clearer and more comprehensible, the present disclosure will be further described below in conjunction with the accompanying drawings and examples. The embodiments described below are some rather than all of the embodiments of the present disclosure. All other embodiments derived from the embodiments of the present disclosure by those of ordinary skill in the art without creative efforts should fall within the protection scope of the present disclosure.

For ease of understanding the technical processes of the embodiments of the present disclosure, some nouns involved in the embodiments of the present disclosure are explained below.

A pharmacophore model is an abstract description of a molecular feature, including spatial information and functional group required for a molecule to bind to a particular target. According to the build methods, pharmacophores can be divided into two types: one is based on receptor structural information, analyzing the interaction patterns between receptors and drug molecules to infer possible pharmacophore structures. The other type is applicable when the receptor structure is unknown or the mechanism of action is not clear. In this case, pharmacophore studies are conducted on a series of compounds using methods such as conformational analysis and molecular superimposition to deduce the information about key functional groups that play a crucial role in the compounds' activity.

A bioactive molecule refers to a molecule that can bind to a specific target and exhibit a therapeutic potential.

A simplified molecular input line entry specification (SMILES) is a specification for representing a chemical structure of a molecule with an American standard code for information interchange (ASCII) string.

The method for generating a small molecule based on a pharmacophore model provided in the present disclosure and an application scenario thereof are described below.

Step 1, a fully connected graph is used to represent a given pharmacophore model.

Figure 1:
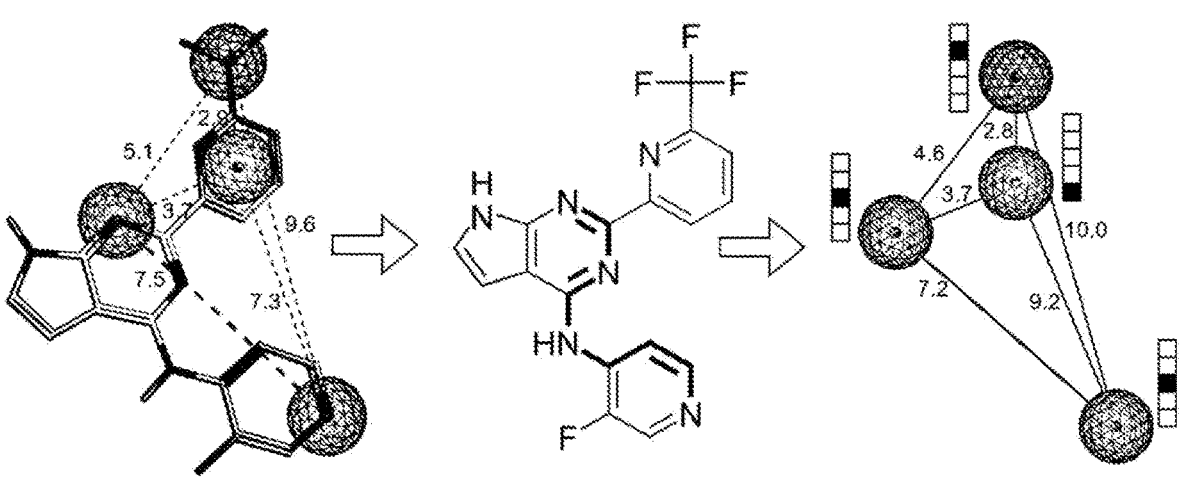
FIG. 1 is a code pattern of a pharmacophore model according to an embodiment of the present disclosure.

That is, the given pharmacophore model is transformed into the fully connected graph according to the following rule: G={V, E}. As show in FIG. 1, V is a set of nodes. Each node in V corresponds to one pharmacophore feature in the pharmacophore model, and attributes of the node are a type and a shape of the corresponding pharmacophore feature. E is a set of edges. A edge is connected between every two nodes, and an attribute of each edge is a distance between the pharmacophore features indicated by nodes at two ends.

In the present embodiment, a path between centers of the pharmacophore features and a type of a chemical bond are mainly taken into account in calculating the distance between the pharmacophore features. A molecule is composed of a single atom or a plurality of different atoms, and atoms are connected to each other by a chemical bond. This method uses lengths of different types of chemical bonds to represent a distance between two atoms. The types and number of chemical bonds (of which the lengths are affected by the types) have a great influence on the distance between the pharmacophore features. Therefore, in the present embodiment, the sum of the lengths of the chemical bonds connecting two pharmacophore features is used to measure the distance between the pharmacophore features. In the present embodiment, the path is a connection mode between the pharmacophore features. Considering that there may be a plurality of connection modes between two pharmacophore features, the shortest path connecting two feature elements is selected herein. The lengths of all chemical bonds between two pharmacophore features are calculated as candidate distances, and a shortest distance is selected therefrom as the distance between every two pharmacophore features.

Step 2, a feature extraction model based on a graph neural network is used to extract a feature vector of the pharmacophore model from the fully connected graph of the pharmacophore model.

In the present embodiment, a gated graph convolution network (Gated GCN) is used to extract a feature of the pharmacophore model. Thus, the information of edges is encoded into the node features, and the resulting feature vector of the pharmacophore model is a repeatable set of feature vectors of the pharmacophore features.

Step 3, random sampling is performed on a specified prior distribution of latent variables to obtain a latent variable, where the latent variables will be described in the specific explanation of step 4.

Step 4, the latent variable and the feature vector of the pharmacophore model are input to a pre-trained decoder to generate a molecule matching the pharmacophore model.

1. An Algorithm Model for Generating a Molecule

Since the pharmacophore model is in a many-to-many relationship with a molecule, a latent variable z is introduced in the present disclosure, and a molecule m is uniquely encoded as a combination of two parts: $(c_p, z)$. $c_p$ represents the given pharmacophore model, and z represents how chemical components in the pharmacophore model express and are combined into a molecule. Thus, the following probability model is established:

$$P(m \mid c_p) = \int_{z \sim P(z \mid c_p)} P(m \mid c_p, z) P(z \mid c_p) dz$$

The probability model is expressed by using an variational autoencoder in the present disclosure, where $P(z \mid c_p, m)$ is fitted by training an encoder, and $P(m \mid c_p, z)$ is fitted by training a corresponding decoder, and a prior distribution of latent variables z is specified. In some use examples, the prior distribution may be a standard normal distribution.

Figure 2:
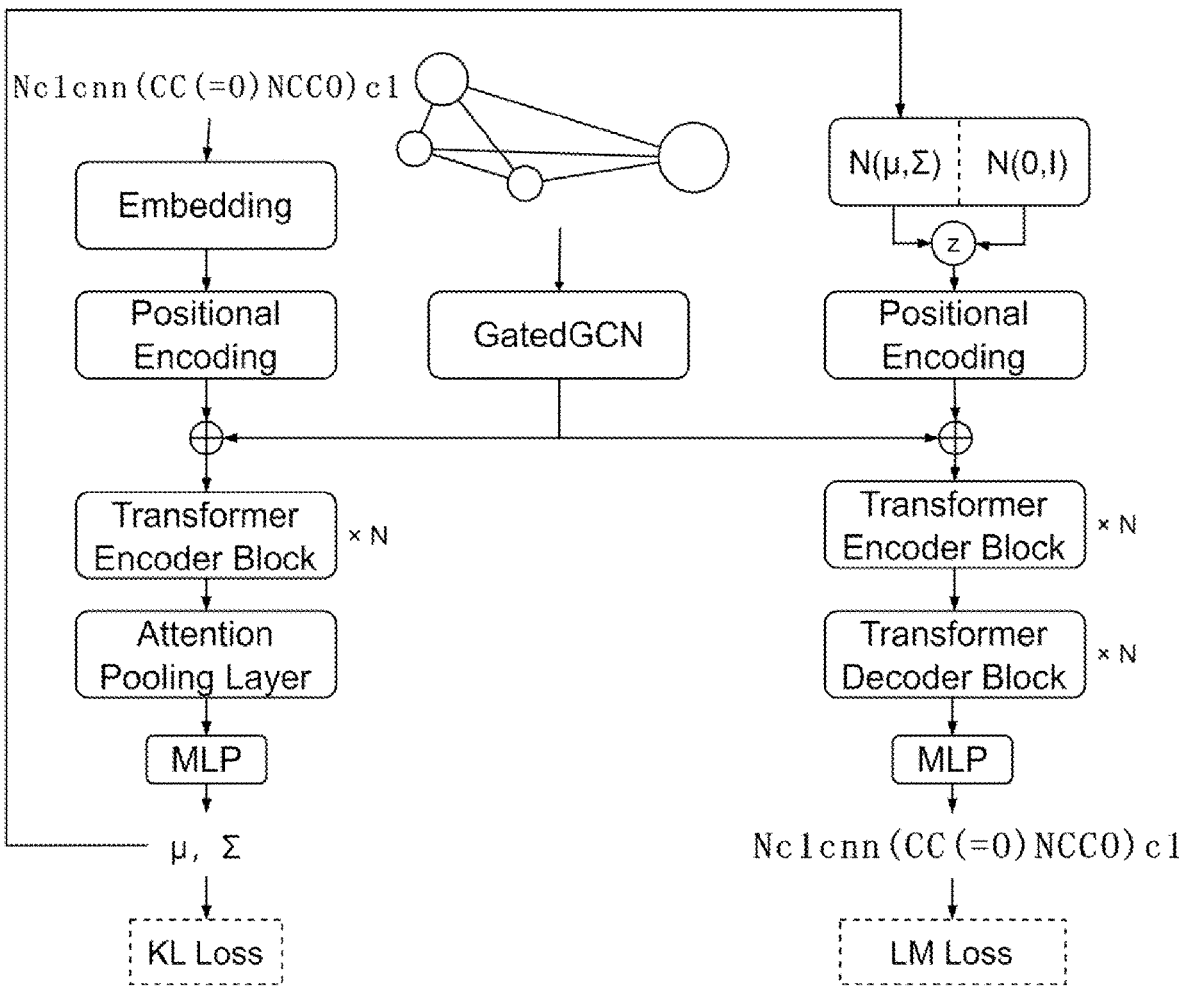
FIG. 2 is a schematic diagram of training a molecular generative model according to an embodiment of the present disclosure.

The variational autoencoder includes an encoder, a decoder, a prior distribution of latent variables, and a loss function, where the encoder and the decoder are constructed by using a Transformer architecture. An input-output relationship for the variational autoencoder during training is as shown in FIG. 2:

The feature vector of the pharmacophore model and the molecule matching the pharmacophore model are input to the encoder to obtain a latent variable distribution of the molecule with respect to the pharmacophore model.

A latent variable is sampled from the latent variable distribution output from the encoder, and the feature vector of the pharmacophore model and the sampled latent variable are input to the decoder to generate a molecule by an iterative loop.

The prior distribution of latent variables is used for performing minimal optimization on a difference between the latent variable distribution obtained by the encoder during training and a given prior distribution.

The loss function is used for quantizing a difference between the molecule generated by the decoder and the molecule in the training samples.

2. Model Training Samples

The training samples for the variational autoencoder include the feature vector of the pharmacophore model and the molecule matching the pharmacophore model. An approach for creating the training samples in the present embodiment is as follows.

(1) Data of Active Molecules is Acquired

Alternatively, 1.25 million molecules of ChEMBL24 data set are used to train the model in the present embodiment, and data is filtered depending on whether the molecular weight of the molecule is greater than 150 and less than 500. Finally, the data set contains 13 types of atoms (H, B, C, N, O, F, Si, P, S, Cl, Se, Br, and I) and five types of chemical bonds (no bond, single bond, double bond, triple bond, or aromatic bond).

In the present embodiment, molecules are expressed by using the SMILES, and each molecule is expressed as a SMILES string, and word segmentation is carried out.

Specifically, the word segmentation is carried out by using regular expression \[[/\\]]+\]|B[r]?|C[1]?|N|O|P|S|F|I|[bcn-ops]|@@|@|%\d{2}|. Each continuous string complying with the expression may be taken as a word, and then a word sequence is obtained. For example, C(C[NH2-])OC(=O)Cl may be transformed into C/(/C/[NH2-]/)/O/C/(/=/O/)/Cl. Subsequently, a special word [SOS] marking a start is added to the head of the word sequence, and a special word [EOS] marking an end is added to the end. By letting each word correspond to a learnable low-dimensional dense vector, a molecule may be transformed into a vector sequence. Since the Transformer architecture used in this example cannot directly identify sequence information, a vector at each position of the molecular sequence is let to be the sum of a vector corresponding to the original word and a position vector. Any vector sequence mentioned below is added with a position vector.

(2) A Pharmacophore Model is Acquired

1) All pharmacophore features of a given molecule are obtained. Alternatively, this step is performed by using RDKit2019. The pharmacophore features are defined by the Basefeatures.fdef given by RDKit, which includes a series of defined molecular substructures and respective pharmacophore features thereof. Basefeatures.fdef is used to acquire all the pharmacophore features of a molecule in the present disclosure. Common pharmacophore features include an aromatic ring center, a hydrophobic, a positive charge center, a hydrogen bond receptor, and a hydrogen bond donor. A negative charge center and ZnBinder are relatively rare and thus set as unknown labels in the present disclosure.

2) Based on experience, a pharmacophore model is generally composed of 3-7 pharmacophore features. Therefore, in the present embodiment, 3-7 pharmacophore features are randomly picked up from all the pharmacophore features obtained in 1) as the pharmacophore model for each molecule.

3) By the same approach in step 2, the feature extraction model based on the graph neural network is used to extract a feature vector of the pharmacophore model from the fully connected graph of the pharmacophore model, which is actually a repeatable set of feature vectors of the pharmacophore features.

3. Training of the Variational Autoencoder

1) After the above training samples are obtained, the vector sequence transformed from the molecule and the repeatable set of feature vectors of the pharmacophore features are input to the encoder to calculate a distribution of latent variable vectors, and a latent variable vector is sampled therefrom.

2) The latent variable vector and the repeatable set of feature vectors of the pharmacophore features are input to the decoder to obtain a probability distribution of a first word.

3) The latent variable vector and the repeatable set of feature vectors of the pharmacophore features as well as feature vector sequences of words of the first N input molecules are input to the decoder to obtain an estimated probability distribution of the (N+1)th word, and a word with the maximum probability is taken as the generated word. This process is repeated until N is equal to the length of the input molecular sequence.

4) The loss function of the model is calculated according to the probability distribution of the word in step 3) and the word at each position on the input string as well as the latent variable distribution calculated in step 1) and the standard normal distribution, and model parameters are updated by using a gradient descent method.

After a plurality of rounds of training, a trained variational autoencoder can be obtained, where the decoder may be employed to generate an active small molecule according to the feature vector of the pharmacophore model in step 4.

4. Use of the Pre-Trained Decoder to Generate a Small Molecule

1) For a protein target having a bioactive molecule, a pharmacophore model is obtained by conformation superimposition of the active molecule. For a known target structure, a binding site of a protein and a ligand is analyzed according to a three-dimensional structure of the target, and a pharmacophore model is established.

2) According to step 1, the acquired pharmacophore model is transformed into graph $G=\{V, E\}$.

3) According to step 2, the graph established based on the pharmacophore model is input to the gated GCN, and the information of edges is encoded into node features to obtain a repeatable set of node feature vectors, denoted as a feature vector of the pharmacophore model.

4) A latent variable is sampled from the latent variable distribution obtained by training.

5) The latent variable vector and the feature vector of the pharmacophore model are input to the decoder to obtain a probability distribution of a first word.

6) The latent variable vector and the feature vector of the pharmacophore model as well as feature vector sequences of words of the first N input molecules are input to the decoder to obtain an estimated probability distribution of the (N+1)th word, and a word with the maximum probability is taken as the generated word. This process is repeated until N is equal to a large enough preset value, and the molecule generated by the given pharmacophore model is obtained.

5. Verification and Application of a Generation Result

1) Detection on a generated new molecule involves the novelty, uniqueness, and effectiveness of the generated molecule.

Firstly, a generated molecule data set is filtered by the validity, uniqueness, and novelty. Specifically, a valid molecule refers to a chemically valid molecule without breaking the chemical valence bond rule in the present disclosure. A unique molecule refers to a non-repetitive molecule generated in the present disclosure. A novel molecule refers to a generated molecule that is not present in a training set in the present disclosure. For a molecule meeting requirement, the molecule will be subjected to next step to inspect whether the generated molecule matches the pharmacophore model.

2) Whether the generated molecule matches the pharmacophore model is inspected.

A molecule may have many chemical features, and a subset thereof may be regarded as a pharmacophore model. In the present embodiment, all the chemical features of a molecule are transformed into a fully connected graph. The problem of calculating a matching degree between a given molecule and a given pharmacophore model may be regarded as finding a best match for a small graph from a large graph. Since the generated molecule usually contains few heavy atoms, the matching degree is calculated using a brute force algorithm in this experiment. Calculation steps are as follows:

a) A set T of all pharmacophore features in the generated molecule is extracted by using RDKit.

b) The input set T of pharmacophore features is classified according to types of pharmacophore features of a reference pharmacophore model to obtain [t1,t2, . . . , tn], where t1 represents a set of pharmacophore features of a first type.

c) A pharmacophore feature is extracted from each of different types of the classified set of pharmacophore features [t1, t2, . . . , tn] each time to form a pharmacophore model G'. A distance $D_q$ between every two pharmacophore features are calculated according to step 2, and compared with a distance $D_r$ between corresponding reference pharmacophore features. If $|D_r{-}D_q|{<}1.2$, the distance $D_q$ is considered to meet the distance between corresponding pharmacophore features of the reference pharmacophore model.

d) The number $match_{num}$ of the edges meeting the distance between the reference pharmacophore features is recorded.

e) For each G' in c), $$\text{match score} = \frac{match_{num}}{match_{all}},$$

where $match_{all}$ represents the number of all edges in G'.

f) Steps c) to e) are repeated, a maximum match score is output as the matching degree of the generated molecule with the reference pharmacophore model.

Figure 3:
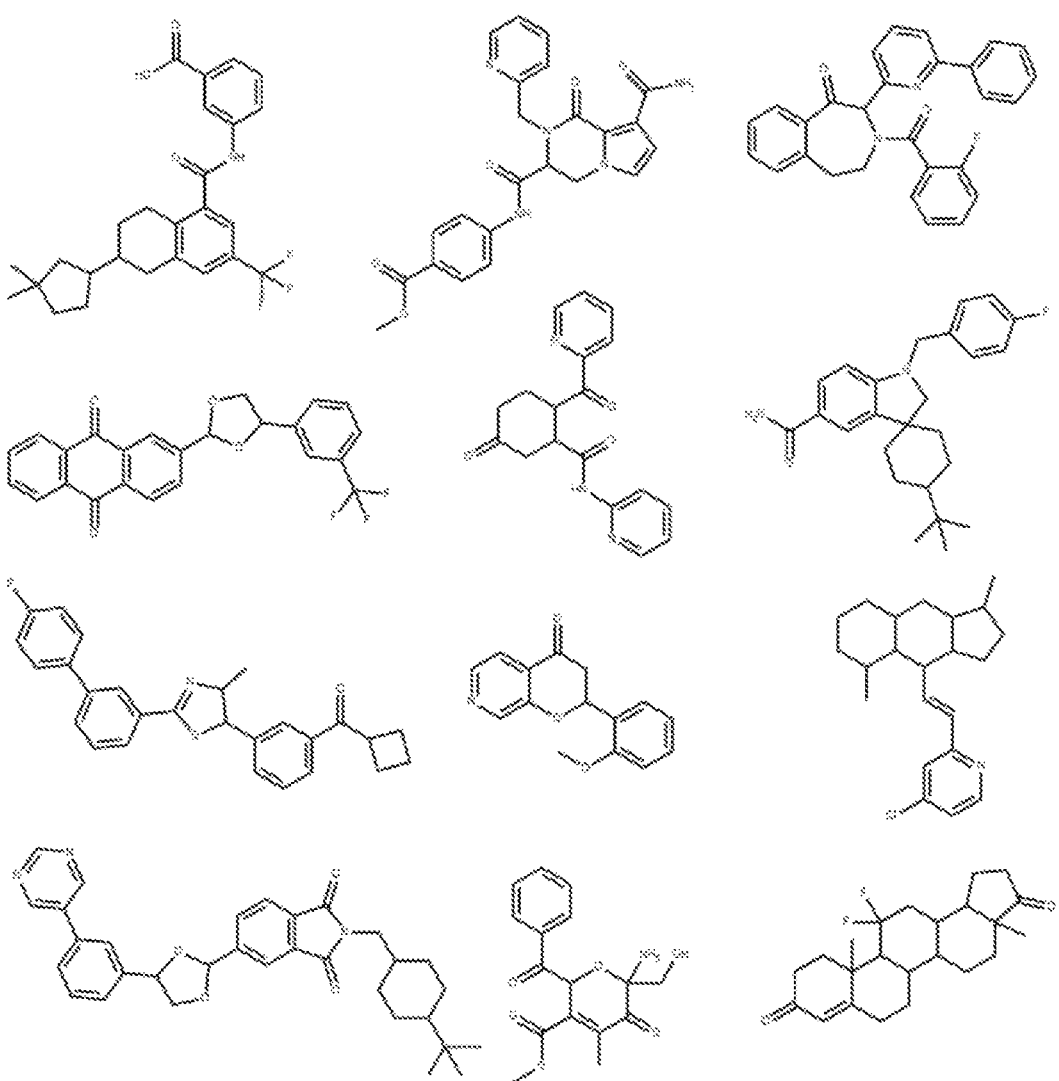
FIG. 3 illustrates molecule structures according to an embodiment of the present disclosure.

3) Candidate results are output for an entity experiment of next stage, and part of molecules generated by the method are as shown in FIG. 3.

Molecules having a matching degree of greater than 0.8 are output as candidate molecules obtained based on the given pharmacophore model. The embodiment of the present disclosure is intended to, for a protein target having a bioactive molecule, obtain a pharmacophore model by conformation superimposition of the active molecule and design a new active molecule; or for a known target structure, a binding site of a protein and a ligand is analyzed according to a three-dimensional structure of the target. A new molecule likely to have a biological activity is generated by the pharmacophore model established according to the binding site. Moreover, since the present disclosure can generate thousands of molecules having a matching degree of greater than 0.8 and different in molecular structure according to a given pharmacophore model, the present disclosure may also be applied to create a virtual screening ligand molecule library, thereby improving the efficiency of virtual screening. The present disclosure is intended to provide a method for rapidly designing an active molecule and improve the efficiency of lead compound discovery, but cannot replace a biochemical experiment, an animal experiment, a clinical experiment, and the like for new drug research and development. A new drug research and development needs to complete subsequent experiments to obtain a final new drug molecule.

The foregoing embodiments are preferred embodiments of the present disclosure. Various changes or improvements can be made by those of ordinary skill in the art on this basis, and without departing from the general concept of the present disclosure, these changes or improvements should fall within the protection scope of the present disclosure.

What is claimed is:

1. A method for generating a small molecule based on a pharmacophore model, comprising:

step 1, using a fully connected graph to represent a pharmacophore model;

step 2, using a feature extraction model based on a graph neural network to extract a feature vector of the pharmacophore model from the fully connected graph of the pharmacophore model;

step 3, performing random sampling on a specified prior distribution of latent variables to obtain a latent variable; and step 4, inputting the latent variable and the feature vector of the pharmacophore model to a pre-trained decoder to generate a molecule matching the pharmacophore model;

wherein the pre-trained decoder is a decoder obtained by training a variational autoencoder with training samples; and the variational autoencoder is expressed as:

$$P(x \mid c) = \int_{z \sim P(z|c)} P(x \mid c, z)P(z \mid c)dz;$$

wherein $P(x|c)$ represents the variational autoencoder, and $P(z|c, x)$ and $P(x|c, z)$ represent an encoder and a decoder forming the variational autoencoder, respectively; x represents a molecule, which is uniquely encoded as a combination of the feature vector c of the pharmacophore model and a latent variable z; and the latent variable z represents a way of the pharmacophore model mapping to the molecule, namely how chemical components in the pharmacophore model express and are combined into the molecule;

wherein the variational autoencoder comprises an encoder, a decoder, a prior distribution of latent variables, and a loss function; the training samples for training the variational autoencoder comprise the feature vector of the pharmacophore model and the molecule matching the pharmacophore model; upon training the variational autoencoder with the training samples:

the feature vector of the pharmacophore model and the molecule matching the pharmacophore model are input to the encoder to obtain a latent variable distribution of the molecule with respect to the pharmacophore model;

a latent variable is sampled from the latent variable distribution output from the encoder, and the feature vector of the pharmacophore model and the sampled latent variable are input to the decoder to generate a molecule by an iterative loop;

the prior distribution of latent variables is used for performing minimal optimization on a difference between the latent variable distribution obtained by the encoder during training and a given prior distribution; and the loss function is used for quantizing a difference between the molecule generated by the decoder and the molecule in the training samples.

2. The method for generating a small molecule based on a pharmacophore model according to claim 1, wherein the loss function comprises but is not limited to two parts; an expression of a first part is $-KL(P_\varphi(z|x,c)|P_\theta(z|c))$, wherein $\varphi$ represents a decoder parameter, and $\theta$ an encoder parameter, z the latent variable, x the molecule, c the pharmacophore model, and KL Kullback-Leibler divergence; and an expression of a second part is $logP_\theta(x|z,c)$.

3. The method for generating a small molecule based on a pharmacophore model according to claim 1, wherein the encoder and the decoder are based on a Transformer architecture.

4. The method for generating a small molecule based on a pharmacophore model according to claim 1, wherein the using a fully connected graph to represent a pharmacophore model specifically comprises forming the fully connected graph of the pharmacophore model with each pharmacophore feature comprised in the pharmacophore model as a node and associated information between the pharmacophore features as an edge, wherein a node feature comprises but is not limit to a type and a shape of the pharmacophore feature.

5. The method for generating a small molecule based on a pharmacophore model according to claim 4, wherein a length of a shortest path between the pharmacophore features is used to represent an association relationship between the pharmacophore features.

6. The method for generating a small molecule based on a pharmacophore model according to claim 1, wherein the given prior distribution is specifically a standard normal distribution.

7. The method for generating a small molecule based on a pharmacophore model according to claim 1, wherein the molecule in the training samples and the molecule generated in step 4 are expression forms obtained after performing an original molecule by using a simplified molecular input line entry specification (SMILES).

8. An electronic device, comprising a memory in which a computer program is stored, and a processor, wherein the computer program, when executed by the processor, causes the processor to implement the method according to claim 1.

9. The electronic device according to claim 8, wherein the loss function comprises but is not limited to two parts; an expression of a first part is $-KL(P_{\varphi}(z|x,c)|P_{\theta}(z|c))$, wherein $\varphi$ represents a decoder parameter, and $\theta$ an encoder parameter, z the latent variable, x the molecule, c the pharmacophore model, and KL Kullback-Leibler divergence; and an expression of a second part is $\log P_{\theta}(x|z,c)$.

10. The electronic device according to claim 8, wherein the encoder and the decoder are based on a Transformer architecture.

11. The electronic device according to claim 8, wherein the using a fully connected graph to represent a pharmacophore model specifically comprises forming the fully connected graph of the pharmacophore model with each pharmacophore feature comprised in the pharmacophore model as a node and associated information between the pharmacophore features as an edge, wherein a node feature comprises but is not limit to a type and a shape of the pharmacophore feature.

12. The electronic device according to claim 11, wherein a length of a shortest path between the pharmacophore features is used to represent an association relationship between the pharmacophore features.

13. The electronic device according to claim 8, wherein the given prior distribution is specifically a standard normal distribution.

14. The electronic device according to claim 9, wherein the molecule in the training samples and the molecule generated in step 4 are expression forms obtained after performing an original molecule by using a simplified molecular input line entry specification (SMILES).

15. A non-transitory computer-readable storage medium, which stores a computer program thereon, wherein the computer program, when executed by a processor, implements the method according to claim 1.

16. The computer-readable storage medium according to claim 15, wherein the loss function comprises but is not limited to two parts; an expression of a first part is $-KL(P_{\varphi}(z|x,c)|P_{\theta}(z|c))$, wherein $\varphi$ represents a decoder parameter, and $\theta$ an encoder parameter, z the latent variable, x the molecule, c the pharmacophore model, and KL Kullback-Leibler divergence; and an expression of a second part is $\log P_{\theta}(x|z,c)$.

17. The computer-readable storage medium according to claim 15, wherein the encoder and the decoder are based on a Transformer architecture.

* * * * *